United States Patent [19]

Grimson

[11] Patent Number: 4,827,216

[45] Date of Patent: May 2, 1989

[54] DIFFERENTIAL TRIPLE-COIL TESTER FOR WIRE ROPE WITH PERIODIC LAY EFFECT CANCELLATION

[76] Inventor: E. G. Grimson, 6712 Neddy Ave., Canoga Park, Calif. 91307

[21] Appl. No.: 30,666

[22] Filed: Mar. 25, 1987

[51] Int. Cl.[4] .................... G01N 27/82; G01N 27/90
[52] U.S. Cl. .................... 324/241; 73/160; 324/225; 340/677
[58] Field of Search .................... 324/206, 219–221, 324/233, 239–243, 225; 73/159, 160; 340/675–677; 356/430

[56] References Cited

U.S. PATENT DOCUMENTS

| | | | |
|---|---|---|---|
| 2,065,119 | 12/1936 | Davis | 324/241 |
| 2,582,437 | 1/1952 | Jezewski et al. | 324/241 |
| 2,746,012 | 5/1956 | Price | 324/242 |
| 3,020,472 | 2/1962 | Cauley | 324/242 X |
| 3,020,473 | 2/1962 | Cauley | 324/233 |
| 3,146,395 | 8/1964 | Quittner | 324/241 |
| 4,058,962 | 11/1977 | Spescha et al. | 73/160 X |
| 4,263,551 | 4/1981 | Gregory et al. | 324/233 |
| 4,423,377 | 12/1983 | Podhrasky | 324/239 X |
| 4,538,107 | 8/1985 | Varone | 324/242 X |

FOREIGN PATENT DOCUMENTS

| | | | |
|---|---|---|---|
| 0186964 | 7/1986 | European Pat. Off. | 324/220 |
| 0001533 | 1/1980 | Japan | 324/242 |
| 0110048 | 9/1981 | Japan | 324/220 |

Primary Examiner—Gerard R. Strecker
Attorney, Agent, or Firm—Ashen Golant Martin & Seldon

[57] ABSTRACT

An electrical coil driven by an alternating current develops an alternating magnetic field. A segment of a wire-rope specimen is placed next to and on the axis of the coil, but perpendicular to the axis, so that the specimen lies in the field. Two sensor coils detect the field on the opposite side of the specimen from the field coil. The sensor coils are mutually conaxial, and paraxial with the specimen. The sensor coils are spaced apart very slightly, along the length of the specimen—one in each direction from the field-coil axis. Each sensor coil is asymmetric, in the shape of a "D," with its sensitive axis just within the "D" but nearer to the flat side; the specimen is placed just outside the "D" but also next to the flat side. Alternating current induced in the sensor coils are applied to the respective input terminals of a differential amplifier, producing an output signal in which the common signal components tend to cancel out. The residual signal is accordingly insensitive to uniform characteristics of the specimen, but sensitive to local variations such as localized defects. The alternating output of the differential amplifier is sampled at an adjustable phase point, selected to vary the display mode for the specimen material at hand.

19 Claims, 4 Drawing Sheets

FIG. 1
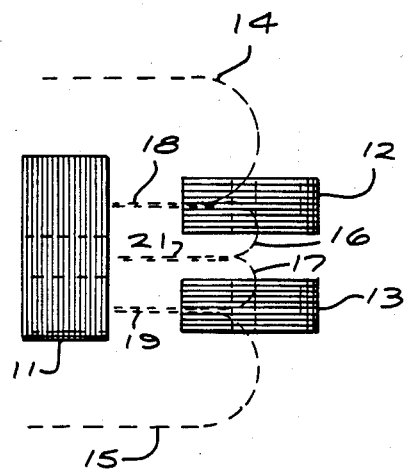
FIG. 2
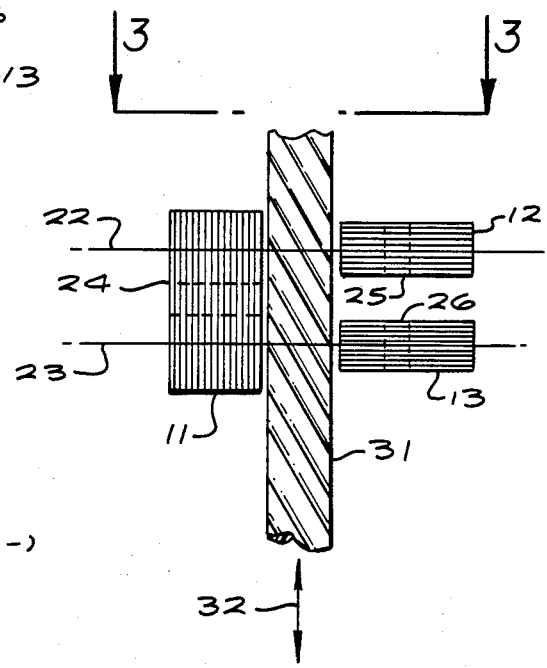
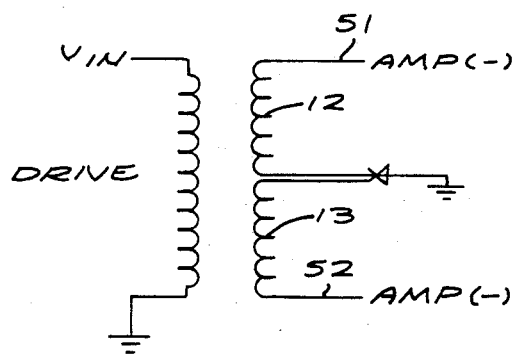
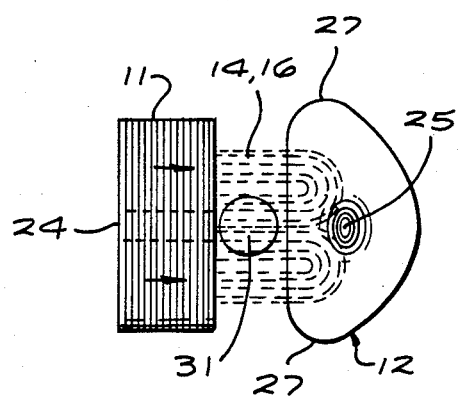
FIG. 4
FIG. 3

4,827,216

DIFFERENTIAL TRIPLE-COIL TESTER FOR WIRE ROPE WITH PERIODIC LAY EFFECT CANCELLATION

BACKGROUND

1. Field of the Invention

This invention relates generally to apparatus for locating mechanical defects in a specimen having an extensile direction, such as a wire rope; and more particularly to an improved tester that is relatively insensitive to uniform characteristics such as the material and lay of a wire rope—and accordingly is relatively more sensitive to small defects.

2. Prior Art

Wire rope is used in myriad industrial applications—notably including control cables in aircraft and support cables for elevators, hanging scaffolds and cranes, and mining equipment. In many, if not the great majority, of such applications, lives as well as costly equipment depend immediately upon the integrity of the wire rope.

Until about a dozen years ago, however, the only commercially available testing method for such relatively small-diameter wire rope was primitive. It consisted of a manual "rag wipe" of the rope to feel for broken wires and loose wire bundles ("bird caging"), supplemented by a close visual inspection for corrosion.

Such a method fails to detect many internal defects such as internal breakage, bird caging, corrosion, wear, and work hardening. In fact, even external wear and corrosion are often overlooked in such testing. Nevertheless this method is still commonly used throughout industry.

Electromagnetic testing of wire rope has been attempted since the early 1800's, using several different sensor arrangements. As far as I know, these devices were all directed to inspecting rope of relatively large diameter—one to three inches—used primarily in mines. The sensitivity of these devices was relatively coarse.

In 1975, however, I introduced a wire-rope tester that operates on an electromagnetic principle. It consists of a field-developing coil, a split sensor coil, and electronic circuitry for energizing the field coil and detecting fluctuations in the current from the sensor coil.

The sensor coil, though it has a gap in which a segment of the wire rope is positioned, is wound as a single coil. Its two sections are conaxial with each other and with the field coil.

The electronics in my prior tester includes a "tuned tank" circuit, in which the uniform component of the cable reluctance contributes to the tank frequency. Therefore the testing instrument is preliminarily tuned for each new wire-rope specimen.

That testing instrument has been adopted by the U.S. Air Force, Coast Guard, and Navy—and many foreign military services as well—as the required method of control-cable inspection on the C-130 aircraft and others. Accordingly the instrument has saved the lives of innumerable crew members and passengers.

That instrument does, however, have certain limitations. First, because of the sensor arrangement and type of circuitry employed, the largest rope that can be inspected is approximately 5/32 inch in diameter.

Secondly, when a wire rope is passed through the probe, the periodic structure or "lay" of the rope causes pulses in the detection circuit. Such pulses are—but for their periodicity—indistinguishable from those caused by small localized defects. This effect limits the sensitivity of the instrument to such defects.

The prior art consequently leaves room for improvement in the field of wire-rope testing.

SUMMARY OF THE DISCLOSURE

The invention is an apparatus for locating a mechanical defect in a specimen having an extensile direction.

The apparatus must include some means for developing a field. For purposes of generality in expression, I shall refer to these means as "field-developing means."

The invention also includes some means for producing a pair of individual signals related to the character of the field at two separate locations. Again in the interest of generality I shall refer to these means as "dual signal-producing means."

The dual signal-producing means are both responsive to the field, and they are disposed at the two separate locations of interest.

The field-developing and signal-producing means are adapted and mutually disposed to accommodate disposition of a segment of the specimen in the field. The specimen operates to perturb the field at the two locations of interest.

The field and signal means are also adapted and disposed for movement of the specimen, along its extensile direction, through the field. It will be understood that what is important in this connection is actually relative movement of the specimen with regard to the apparatus, to bring all the segments of the specimen successively into probing position. Therefore, for purposes of the appended claims, movement of the field and signal means relative to the specimen shall be considered equivalent to movement of the specimen through the field.

The invention must also include some means, responsive to the pair of individual signals, for deriving a composite signal. This derivation is performed in such a way that signal components common to the individual signals tend to cancel out of the composite. I shall refer to these means as the "signal-processing means." The signal-processing means are connected to receive the individual signals.

Finally my invention includes what I shall call "utilization means." The utilization means are responsive to the composite signal, and make use of the composite signal.

The foregoing passage may be a definition of my invention in its most general form. Next I shall describe certain specific features which I prefer to incorporate in the invention for greatest advantage.

In such preferred forms of the invention, the field is a magnetic field—and the field-developing means include an electrical coil for developing the magnetic field, and electronic means for providing an electrical current to excite the coil.

Further, the individual-signal producing means preferably include a pair of electrical coils, sensitive to the magnetic field at the two locations respectively. They produce respective electrical signals related to the magnetic field at the two locations.

The signal-processing means in such preferred embodiments of the invention include electrical circuitry for receiving and processing the electrical signals. The utilization means include an electrical device for indicating or recording deviations in the composite signal, or for both indicating and recording such deviations.

I prefer to use electrical circuitry (such as a differential amplifier or a programmed digital-logic circuit) that subtracts one individual signal from the other—or, more generally, subtracts the value of one individual signal from the value of the other. The preferred circuitry thereby derives a composite signal related to the difference between the two signals.

My invention also, however, encompasses circuitry that instead divides the value of one signal by the value of the other. Such circuitry thereby derives a composite signal related instead to the ratio of the two signals.

I prefer to use current-providing means that provide a current which is periodic, so that the magnetic field likewise is periodic—and the individual signals are also periodic. I also prefer to include in the electrical circuitry at least one adjustable sample-and-hold circuit, so that the composite signal can be derived in response to only selected portions of the individual-signal waveforms.

Through use of a sample-and-hold circuit my invention can be made to derive the composite signal only in response to the individual signals in selected phases of their period. Making the sample-and-hold circuit adjustable permits adaptation of the apparatus to produce displays of different polarity for specimens of different materials. In this way the display polarity emphasizes to the operator what material is being tested.

In the apparatus configuration which I prefer, the signal-producing coils are end-to-end, with a slight gap between them, and the field-developing coil is adjacent to this gap—at the sides of the two signal-producing coils. Thus the signal-producing or "sensor" coils are in essence conaxial mutually, but not with the field coil; this is one major departure from the configuration of my prior tester. By "conaxial" I mean, as illustrated in the accompanying drawings, sharing a common axis but spaced apart along the common axis rather than being one inside the other.

In the preferred configuration there is also another gap, differently oriented, between the field-developing coil and the sides of the two sensor coils. The wire-rope specimen is disposed, paraxial with the sensor coils, in this latter gap. By "paraxial" I mean, as illustrated in the accompanying drawings, having mutually parallel axes. Thus the specimen is next to the end of the field-developing coil, but beside the two signal-producing coils.

The field-developing coil and both signal-producing coils preferably have substantially the form of geometric cylinders. By a geometric cylinder I mean a geometric figure defined as the locus of some two-dimensional shape displaced in a third dimension.

As a matter of standard definition, when such displacement is perpendicular to the plane of the two-dimensional figure the resulting locus is called a "right cylinder." For the sake of simplicity and economy I have employed only right-cylindrical shapes for the coils of my invention, but as far as I know other cylindrical forms would serve.

Also as a matter of standard definition, when the two-dimensional figure is a circle the locus is a "circular cylinder." Again for economy I have used only a circular-cylinder shape for the field-developing coil, but I believe that other cylindrical types would be usable.

If the field-developing coil is not formed as a right-circular cylinder, but still has substantially the form of some other type of geometric cylinder, I prefer to orient the extensile direction of the specimen substantially perpendicular to the direction of production of that type of geometric cylinder. If the coil is not cylindrical, in any event I prefer to position the specimen at the greatest concentration of magnetic-field lines, and to orient the extensile direction of the specimen substantially perpendicular to the magnetic-field lines there.

The signal-producing coils of my invention, however, I prefer to form as noncircular cylinders. The reason for this difference is that, as just mentioned, in the preferred apparatus configuration the wire-rope specimen is next to one end of the field-developing coil but beside the two signal-producing or "sensor" coils. Good measurement sensitivity requires that the active portions of the coils all be as close as practical to the specimen.

This condition is readily met with a field coil that is circular cylindrical, because the coil is "end-on" to the specimen—but not with the sensor coils, as each of these is side-by-side with the specimen. It is therefore desirable to use asymmetric sensor coils whose sensitivity is concentrated at the edge nearest the specimen.

Accordingly after thought and experimentation I prefer to form each sensor coil as an asymmetric geometric cylinder with an offset axis that is parallel to and within the locus of production of the cylinder. Each sensor coil is most sensitive to the magnetic field along the respective offset axis of that sensor coil.

In more familiar terms, each sensor coil has the form of a cylinder produced by displacement of a shape that is very generally similar to a letter "D." The flat side of the "D" shape is actually curved slightly, and the corners are rounded off; however, for purposes of shorthand reference my preferred sensor coils may be described as having the form of "D cylinders."

If the sensor coils are not in the form of right cylinders, I nevertheless prefer to position the specimen with its extensile direction oriented substantially parallel to the directions of production of the geometric cylinders of both signal-producing coils. If the signal-producing coils are not cylindrical, they should in any event be positioned for maximum sensitivity to the perturbations which the specimen produces in the field.

As previously mentioned, the two signal-producing coils are substantially mutually conaxial. Since these coils are asymmetrical, it may now be appreciated that this statement only has meaning with respect to the offset axes of the coils, along which they have maximum sensitivity.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is a somewhat schematic elevation of the probe assembly of a preferred embodiment of my invention, showing the three coils and also indicating the paths of magnetic lines of force.

FIG. 2 is a similar drawing also showing the wire rope in place, but omitting the magnetic lines.

FIG. 3 is a somewhat schematic plan of the same assembly, taken along the line 3—3 of FIG. 2.

FIG. 4 is a partial electrical schematic showing only a preferred wiring of the two sensor coils.

FIGS. 6a and 6b are complementary sections of a detailed electronic schematic.

DETAILED DESCRIPTION OF THE PREFERRED EMBODIMENTS

Figure 5:
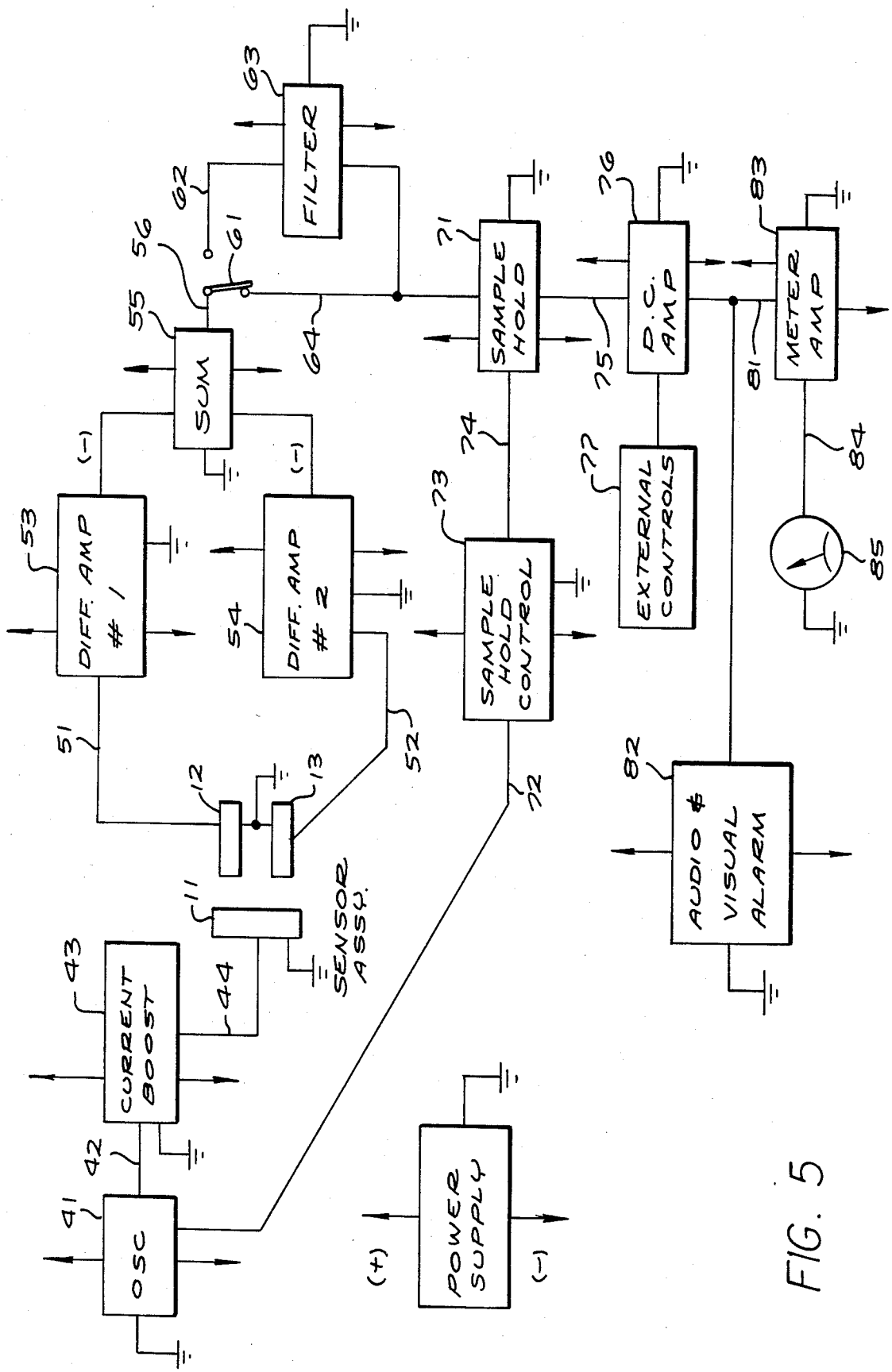
FIG. 5 is a block diagram of the electronics.

As shown in FIGS. 1 through 3, the preferred form of my invention includes a probe consisting of three coils of wire 11, 12 and 13. Their inductances are selected—essentially on the basis of trial and error, but with little time being required—to accommodate different cable diameters.

The field-developing or "driver" coil 11 has the largest inductance. It is energized at some preselected frequency, such as ten kilohertz, to generate a strong alternating magnetic field 14–21 perpendicular to the cable 31 (FIG. 2) being inspected.

The field coil 11 naturally produces a single magnetic dipole, with a very generally dual-toroidal magnetic-field pattern 14–21 that stands out from the coil face about one coil diameter. The dual toroids of the pattern include an outer toroid 14, 15 and an inner toroid 16, 17, 21, which are coaxial and meet at the mean radius 18, 19 of the field coil 11. Considered in elevational cross-section, however, the pattern appears to have two dual lobes—an upper dual lobe 14, 16 and a lower dual lobe 15, 17.

The two sensor coils 12, 13 are arranged at ninety degrees to the driver coil 11 and are roughly centered at the upper and lower mean radii 22, 23 of the field coil 11 respectively—so that each sensor coil 12, 13 intercepts one of the two dual lobes 14, 16 or 15, 17. Once again considering the system in planar section, the overall effect is of two essentially identical magnetic dipoles 14, 16, 18 and 15, 17, 19—each monitored by one sensor coil 12 or 13 respectively.

Thus in effect there are two probe points. Each probe point uses one of the two dual lobes of the magnetic-field pattern, and each has its own sensor coil.

Due to the symmetry of the system, the sensor coils 12, 13 receive substantially equal amounts of magnetic flux. They accordingly produce substantially equal currents. If desired for more-perfect current equalization, they can be adjusted in position—or electrical trimming can be provided.

When a cable 31 is present, it extends through the end region 14–21 of the magnetic-flux pattern, intersecting it twice: once above and once below the field-coil centerline 21. Again viewing the system in planar section, the cable 31 extends through each of the two dual lobes 14, 16, 18 and 15, 17, 19.

When present, such a cable 31 distorts each dual lobe of the field. In each dual lobe, flux lines adjacent to the cable pass through the cable, and the permeability of the cable induces peripheral flux lines to follow new paths. The result is that modified, but still balanced, amounts of magnetic flux pass through the sensor coils 12 and 13.

The sensor coils 12, 13 are on the opposite side of the cable 31 from the driver coil 11. It will be understood that during measurements the cable 31 is kept at the centerline 21 of the driver coil 11 and adjacent to the axes of symmetry of both "D"-shaped sensor coils 12, 13—but naturally the cable 31 is moved or "scanned" along its extensile direction 32 so that in time the entire cable is inspected.

When a defect in the cable 31 enters either effective dual dipole 14, 16, 18 or 15, 17, 19 of the magnetic-field pattern, the interaction of the defect with that effective dual dipole distorts the flux lines in that dual dipole. The result is a change (either positive or negative) in the signal from the corresponding sensor 12 or 13.

This change is directly analogous to the change produced by the presence of the cable 31 in general. If, however, the defect is short compared with the spacing between the sensor coils 12, 13—which is to say, compared with the mean diameter (the distance from 22 to 23 in FIG. 2) of the field coil 11—the signal change appears in only one sensor coil 12 or 13 at a time. The system is now mechanically, magnetically and electronically unbalanced.

As the defect encounters the first dipole-and-sensor probe point along the cable path—i.e., the first field-coil mean radius 22 or 23, depending upon scanning direction—the signal from the corresponding sensor 12 or 13 changes. As the defect leaves that probe point 22 or 23, the change disappears. As the same defect reaches the second dipole-and-sensor probe point 23 or 22 respectively, the change appears in the signal from the second sensor 13 or 12, and then again disappears.

The change in sensor signal due to a relatively minor defect—such as a nick in just a few wires, or corrosion or wire thinning—is greater than might be supposed. In particular the relative change in the signal is much greater than the relative change in the cross-sectional area of the cable 31.

The reason for the greater-than-proportional response is that the high-frequency alternating magnetic field 14–21 interacts with the wire rope 31 by inducing correspondingly high-frequency eddy currents in the rope. By "high-frequency" I mean a frequency very generally on the order of ten kilohertz as previously mentioned. These eddy currents are subject to the well-known skin effect. Surface conditions therefore exert a disproportionately great influence on the overall perturbation of the field by the rope.

I have described what happens in each sensor 12, 13 when the cable 31 is placed in the apparatus, and also what happens as a defect in the cable 31 moves through the probe assembly. Before completing the discussion of system response to defects, it is also important to consider what happens as the cable "lay" moves through the probe assembly.

The cable lay presents a periodic series of bulges and constrictions to the two probe points 22, 23 above and below the assembly centerline 21. Each of these features causes a signal change, in each individual sensor 12 or 13, that is essentially analogous to the above-described changes in response to short defects. As the cable 31 is "scanned" at generally constant speed through the probe assembly, these features produce a regular periodic pulsing in each sensor signal.

There is an important difference, however. In a good cable 31, all the bulges and constrictions are substantially identical to one another. The number of such features instantaneously present at the two probe points 22, 23 therefore tends to be very nearly equal, so that the sensor-signal pulses likewise tend to be almost identical.

As illustrated in FIGS. 4 and 5 the sensor coils 12, 13 are wired differentially—that is, in opposition—so that their two output signals 51, 52 are of opposite sign, not only in the steady state but also for any given discontinuity in the specimen 31.

These sensor-coil output signals 51, 52 are combined to form a composite signal 56. More specifically, they are applied to the inverting inputs of two operational amplifiers 53, 54, and the inverted output is summed and amplified as at 55. Since the coils 12, 13 are wired in opposition, such summing has the effect of subtracting the magnitude of one signal from the magnitude of the other to form the composite signal 56.

The sensor-signal pulses due to rope lay therefore tend to cancel out of the composite 56, provided that they are in phase. If desired for better cancellation in some instances, the spacing between the sensor coils 12 and 13 can be adjusted very slightly to match the periodicity of the rope lay and thereby bring the pulses into phase.

At the same time, to maintain symmetry of flux interception, the sensor coils 12, 13 considered as an array should be kept centered on the driver coil 11. (Alternatively, whatever asymmetry may have been deliberately introduced to balance the system should be maintained.)

The composite signal 56 next proceeds to an oscillating demodulator switch 61, which is in effect part of a sample-and-hold circuit 71. The sample-and-hold circuit 71 and thereby the demodulator 61 are synchronized with the oscillation of the magnetic field by a signal path 72–74 from the same oscillator 41 that drives (at 42–44) the field coil 11. Modern sample-and-hold integrated circuits operate well without the demodulator 61 and associated filter 63, which are accordingly optional.

The phase of the synchronization is adjustable as at 73. Stainless-steel cable is detected using the negative peak of the waveform, and carbon steel using the positive peak. In general the operating phase point of the sample-and-hold circuit 61, 71 is selected to produce a negative-going display for stainless steel and a positive-going display for carbon steel.

The sample-and-hold circuit 71, including the demodulator 61, samples selected points on the waveform of the composite signal 56, 64. This technique amounts to amplitude modulation of a selected portion of the waveform, producing a dc signal 75.

(Equivalently, as will be apparent to those skilled in the art, a separate sample-and-hold circuit could be used in each channel and the resulting sample signals then summed, if that were preferred.)

It is this dc output signal 75 that is used to indicate the cable defects. The dc output 75 is amplified as at 76, with display adjustments controlled at 77, and the amplified signal 81 is transmitted to the meter-amplifier and alarm circuits 83 and 82 respectively.

If the cable 31 under test is not the type for which the sample-and-hold circuit 61, 71 has been adjusted, a warning light or annunciator 82, or both, prompts the operator to correct the setting. Otherwise the twice-amplified signal 84 passes to a meter or other display device 85.

It will be understood that the alarm 82 and display 85 can be replaced or supplemented by other utilization devices for indicating, recording or otherwise using the signal 81. For example, the signal 81 could be used to actuate automatic apparatus for marking defective segments of the cable 31 with various colors of spray paint denoting various defect types or severities.

Now I shall return to the discussion of system response to defects. As just mentioned, the signals 51, 52 from the two sensors 12, 13 are combined in opposition to form a composite signal 56. The overall result of scanning a particular short defect through the probe assembly is therefore a pair of fluctuations in the composite signal 56. First there is an excursion in one direction, and then there is a second excursion in the other direction.

These bipolar excursions in the composite signal 56 serve to identify the positions and magnitudes of defects in the cable. Since the apparatus is a defect detector, the excursions of the composite signal 56 are in effect "the signal" of interest. If desired, this defect signal (that is, the excursions) can be electronically trapped, quantified, and correlated with position along the rope.

The defect signal is extremely "quiet," since the sensor coils 12, 13 are positioned symmetrically in the field pattern 14–21 and wired in a mutually balancing electronic configuration. Consequently a defect signal arises only when a discontinuity is present. To some extent, moreover, the shapes of the excursions can be correlated with known types of defects.

On a theoretical or absolute basis it is difficult to predict what level of excursion should be regarded as "background." In operation, however, scanning of non-suspect cable segments establishes a baseline from which defect signals are measured.

The present system is superior to my previous one in at least three ways. First, with my present apparatus larger cables can be tested. The only limitations on cable size are the size of the magnetic field pattern 14–21 and the diameter of the sensor coils 12, 13.

Coil sizes can be chosen arbitrarily, and coils can be mutually repositioned to accommodate various cable sizes. Consequently the size range is limited primarily by cost.

Secondly, the present system is more sensitive than my earlier one. My new testing apparatus is capable of detecting reliably a fifteen-percent reduction in overall strength of a cable, though a five-percent reduction is easily seen.

These figures are based upon calibration procedures in which artificial defects are installed in a cable. A technician can put such defects in place by locally annealing or hardening a section of the cable with a torch, or by partially disassembling the cable and deliberately damaging it internally before reassembly.

Wire rope is made up of wire bundles. For example, a "seven by seven" cable consists of seven bundles of seven wires each, each individual wire thus representing two percent of the available cable strength. A "seven by nineteen" cable consists of seven bundles of nineteen wires each, each wire providing less than one-half percent of the total strength. The bundles are twisted together to form the cable.

Thus for sensitivity-calibration purposes an internal defect can be provided by unwrapping the outer wire bundles of the cable and modifying the central core bundle. For example, a technician may actually sever the central bundle, and reassemble the outer bundles leaving a small gap in the central one—or may instead grind the individual wires of the central bundle by a measured amount, such as fifty percent, before reassembly.

From the detection limits mentioned above, it will be clear that neither my earlier system nor the present one is capable of detecting individual broken wires in a seven-by-seven or larger cable. Some users of my prior system, however, have developed techniques which seem to permit detection of smaller defects than I have calculated for that apparatus.

A third advantage of my new system is that it is more readily adjusted to accommodate various cable sizes and materials. In the earlier apparatus, as previously mentioned, the cable under test functioned as part of a tuned-tank circuit.

Frequency and amplitude of the energizing waveform therefore required adjustment upon change of cable characteristics. Variable-frequency oscillators are relatively expensive, particularly at the relatively high power levels required to energize a large field coil for testing large cables.

In my new instrument only a display-zero adjustment is required for change of size, and only a sample-and-hold phase adjustment is required for change of material. These are modest electronic adjustments, very economically provided for any cable size.

FIGS. 6a and 6b represent details of the electronics of my invention as I now prefer them. To those skilled in the art, these drawings will be meaningful without further discussion.

Typical inductances for the field and sensor coils 11 and 12, 13 are 0.6 and 0.12 millihenry respectively. These values are suitable for rope diameters between 1/16 and 5/32 inch.

As mentioned earlier, the magnetic field that is produced by the driver coil 11 has in simplest principle a dual-coaxial-toroid shape. When the field coil 11 is operated without a cable specimen 31 in place, a circular or annular node appears in front of the driver coil 11 at the mean radius 18, 19 of that coil. Considering the system in planar section as before, this annular node effectively produces two nodal positions 18 and 19, one above and one below the coil centerline 21.

It might be supposed that the sensor coils 12 and 13 should be well displaced from these nodes 18 and 19 respectively. In practice, however, this precaution is unnecessary. Magnetic-field distortion by a cable specimen 31 renders the field pattern 14–21 very indistinct, essentially eliminating the nodes and obviating this restriction on sensor-coil placement.

For good channel separation the sensor coils 12, 13 must be spaced apart distinctly. I prefer to use a spacing at least equal to the sensor-coil thickness—that is, the dimension parallel to the cable length 32.

I have described my invention as implemented with magnetic fields. I believe, however, that it has application with other types of probe fields, perhaps using Hall-effect or ultrasound sensing. Such systems accordingly may be within the scope of certain of my appended claims.

It will be understood that the foregoing disclosure is intended to be merely exemplary, and not to limit the scope of the invention—which is to be determined by reference to the claims.

I claim:

1. Apparatus for locating a mechanical defect in a wire-rope specimen having an extensile direction and having a known periodic structure along the extensile direction, said apparatus comprising:
   means for developing a field;
   dual means, disposed at two locations near the field-developing means and responsive to the field, for producing a pair of individual signals related to the character of the field at the two locations respectively;
   said field-developing and signal-producing means being adapted and mutually disposed to accommodate disposition of a segment of such a specimen in the field to perturb the field at the two locations, and for movement of such a specimen along its extensile direction through the field;
   signal-processing means, connected to receive and responsive to the pair of individual signals, for deriving a composite signal representative of such mechanical defect, in which signal components common to the individual signals tend to cancel out;
   said dual signal-producing means being spaced apart by a fixed distance related to such specimen's known periodic structure so that such specimen's known periodic structure produces signal components which are common to both individual signals;
   whereby the effect of such specimen's known periodic structure cancels out of the composite signal; and
   utilization means, responsive to the composite signal for localizing such mechanical defect.

2. The apparatus of claim 1, wherein:
   the field-developing means comprise an electrical coil for developing a magnetic field, and electronic means for providing an electrical current to excite the coil;
   the individual-signal producing means comprise a pair of electrical coils, sensitive to the magnetic field at the two locations respectively, for producing respective electrical signals related to the magnetic field at the two locations;
   the signal-processing means comprise electrical circuitry for receiving and processing the electrical signals; and
   the utilization means comprise an electrical device for indicating or recording, or for both indicating and recording, deviations in the composite signal.

3. The apparatus of claim 2, wherein:
   the electrical circuitry derives the composite signal in such a way that the composite signal is related to the difference between the magnitudes of the two individual signals.

4. The apparatus of claim 2, wherein:
   the electrical circuitry derives the composite signal in such a way that the composite signal is related to the ratio of the magnitudes of the two individual signals.

5. The apparatus of claim 2, wherein:
   the current-providing means comprise means for providing a periodic current so that the magnetic field is periodic;
   whereby in operation the individual signals are also periodic; and
   the electrical circuitry comprises at least one adjustable sample-and-hold circuit to derive the composite signal in response to the individual signals in selected phases of their period exclusively;
   whereby through adjustment of the sample-and-hold circuit the apparatus is adaptable for use with specimens of various materials having correspondingly various phase-response characteristics.

6. The apparatus of claim 5, wherein:
   the electrical circuitry derives the composite signal in such a way that the composite signal is related to the difference between the magnitudes of the two individual signals.

7. The apparatus of claim 5, further comprising:
   an electrical filter for smoothing the output of the sample-and-hold circuit.

8. The apparatus of claim 2, wherein:
   the field-developing coil has substantially the form of a geometric cylinder; and such specimen is accommodated with its extensile direction oriented substantially perpendicular to the direction of production of the geometric cylinder of the field-developing coil.

9. The apparatus of claim 2, wherein:
the field-developing coil has substantially the form of a circular cylinder, with a central axis; and
such specimen is accommodated with its extensile direction oriented substantially perpendicular to the axis of the field-developing coil, and intersecting said axis.

10. The apparatus of claim 2, wherein:
each signal-producing coil has substantially the form of a geometric cylinder; and
such specimen is accommodated with its extensile direction oriented substantially parallel to the directions of production of the geometric cylinders of both signal-producing coils.

11. The apparatus of claim 10, wherein:
the directions of production of the geometric cylinders of the two signal-producing coils are substantially mutually parallel.

12. The apparatus of claim 2, wherein:
the field-developing coil has substantially the form of a geometric cylinder;
each signal-producing coil has substantially the form of a geometric cylinder;
each signal-producing coil is oriented with the direction of production of its geometric cylinder oriented substantially perpendicular to the direction of production of the geometric cylinder of the field-developing coil; and
such specimen is accommodated with its extensile direction oriented substantially perpendicular to the direction of production of the geometric cylinder of the field-developing coil, but parallel to the direction of production of the geometric cylinders of both signal-producing coils.

13. The apparatus of claim 2, wherein:
each signal-producing coil has substantially the form of an asymmetric geometric cylinder with an offset axis that is parallel to and within the locus of production of the asymmetric cylinder;
each signal-producing coil is most sensitive to the magnetic field along the respective offset axis; and
such specimen is accommodated with its extensile direction oriented substantially parallel to the axes of both signal-producing coils.

14. The apparatus of claim 13, wherein:
the two signal-producing coils are substantially mutually conaxial.

15. The apparatus of claim 2, wherein:
the field-developing coil has substantially the form of a geometric cylinder;
each signal-producing coil has substantially the form of an asymmetric geometric cylinder with an offset axis that is parallel to and within the locus of production of the asymmetric cylinder;
each signal-producing coil is most sensitive to the magnetic field along the respective offset axis;
each signal-producing coil is oriented with its offset axis substantially perpendicular to the direction of production of the geometric cylinder of the field-developing coil; and
such specimen is accommodated with its extensile direction oriented substantially perpendicular to the direction of production of the geometric cylinder of the field-developing coil, but parallel to the offset axes of both signal-producing coils.

16. The apparatus of claim 15, wherein:
the two signal-producing coils are substantially mutually conaxial.

17. The apparatus of claim 2, wherein:
each signal-producing coil has substantially the form of an asymmetric geometric cylinder whose cross-section is very generally in the shape of a letter "D" with rounded corners, said shape including a very generally flat side and a very generally curved side, and is most sensitive to the magnetic field along an offset axis parallel to and within the locus of production of the asymmetric cylinder and relatively closer to the generally flat side of the "D" shape than to the generally rounded side; and
such specimen is accommodated substantially adjacent to the generally flat sides of the "D" shapes of both signal-producing coils, and with its extensile direction oriented substantially parallel to the axes of both signal-producing coils.

18. The apparatus of claim 17, wherein:
the two signal-producing coils are substantially mutually conaxial.

19. Apparatus for locating a mechanical defect in a wire-rope specimen having an extensile direction, and having a "lay" that presents a known periodic series of bulges and constrictions along the extensile direction; said apparatus comprising:
means for developing a field;
dual means, disposed at two locations near the field-developing means and responsive to the field, for producing a pair of individual signals related to the character of the field at the two locations respectively;
said field-developing and signal-producing means being adapted and mutually disposed to accommodate disposition of a segment of such a wire-rope specimen in the field to perturb the field at the two locations, and for movement of such a wire-rope specimen along its extensile direction through the field;
signal-processing means, connected to receive and responsive to the pair of individual signals, for deriving a composite signal, representative of such mechanical defect, in which signal components common to the individual signals tend to cancel out;
said dual signal-producing means being spaced apart by a fixed distance related to such wire-rope specimen's known periodic lay so that such wire-rope specimen's known periodic lay produces signal components which are common to both individual signals;
wherein the effect of such wire-rope specimen's known periodic lay cancels out of the composite signal; and
utilization means, responsive to the composite signal for localizing such mechanical defect.

* * * * *